United States Patent
Kroepke et al.

(10) Patent No.: US 8,795,699 B2
(45) Date of Patent: Aug. 5, 2014

(54) WASP REPELLENTS

(75) Inventors: Rainer Kroepke, Schenefeld (DE); Jens Schulz, Rellingen (DE); Jens Nielsen, Henstedt-Ulzburg (DE); Stephanie Von Der Fecht, Wedel (DE)

(73) Assignee: Beiersdorf AG, Hamburg (DE)

( * ) Notice: Subject to any disclaimer, the term of this patent is extended or adjusted under 35 U.S.C. 154(b) by 844 days.

(21) Appl. No.: 12/153,099

(22) Filed: May 14, 2008

(65) Prior Publication Data
US 2008/0305135 A1  Dec. 11, 2008

(30) Foreign Application Priority Data
May 31, 2007  (DE) .......................... 10 2007 026 049

(51) Int. Cl.
| | |
|---|---|
| A01N 25/02 | (2006.01) |
| A61K 8/92 | (2006.01) |
| A61Q 17/02 | (2006.01) |
| A01N 43/16 | (2006.01) |
| A61K 8/49 | (2006.01) |
| A61K 8/97 | (2006.01) |
| A01N 37/46 | (2006.01) |
| A01N 65/00 | (2009.01) |
| A61K 8/44 | (2006.01) |

(52) U.S. Cl.
CPC . *A61K 8/44* (2013.01); *A61K 8/922* (2013.01); *A61Q 17/02* (2013.01); *A01N 43/16* (2013.01); *A61K 8/498* (2013.01); *A61K 8/97* (2013.01); *A01N 37/46* (2013.01); *A01N 65/00* (2013.01); *Y10S 424/10* (2013.01); *Y10S 514/919* (2013.01)

USPC .................. 424/405; 424/406; 424/DIG. 10; 514/544; 514/551; 514/617; 514/739; 514/763; 514/919; 514/316

(58) Field of Classification Search
CPC ....... A01N 27/00; A01N 31/02; A01N 37/10; A01N 37/12; A01N 37/16; A01N 37/18
USPC .................. 514/316, 544, 551, 617, 739, 763
See application file for complete search history.

(56) References Cited

U.S. PATENT DOCUMENTS

| | | | |
|---|---|---|---|
| 4,127,672 | A | 11/1978 | Klier et al. |
| 5,556,881 | A | 9/1996 | Grahn Marisi |

(Continued)

FOREIGN PATENT DOCUMENTS

| | | |
|---|---|---|
| DE | 2 246 433 | 4/1974 |
| DE | 196 45 250 | 5/1998 |

(Continued)

OTHER PUBLICATIONS

F. .Marchio: "Insect Repellent 3535", SOWF-Journal, vol. 22, No. 7, 1996, pp. 478-485.

(Continued)

*Primary Examiner* — Neil Levy
(74) *Attorney, Agent, or Firm* — Abel Law Group, LLP

(57) ABSTRACT

A method of repelling wasps, which method comprises using a preparation comprising (a) one or more of ethyl 3-(N-n-butyl-N-acetylamino)propionate, dihydronepetalactone, and extract of catmint, and (b) at least one compound selected from certain perfume ingredients. This abstract is neither intended to define the invention disclosed in this specification nor intended to limit the scope of the invention in any way.

13 Claims, 1 Drawing Sheet

(56) References Cited

U.S. PATENT DOCUMENTS

| | | |
|---|---|---|
| 6,306,905 B1 | 10/2001 | Kurz et al. |
| 6,740,319 B2 | 5/2004 | Aldrich |
| 2003/0109581 A1 | 6/2003 | Aldrich |
| 2004/0092606 A1 | 5/2004 | McPartland |

FOREIGN PATENT DOCUMENTS

| | | |
|---|---|---|
| DE | 196 45 920 | 5/1998 |
| DE | 103 49 666 A1 | 5/2005 |
| DE | 10 2005 033 845 | 1/2007 |
| EP | 1745772 A2 * | 7/2006 |
| EP | 1 745 772 A2 | 1/2007 |
| WO | 98/23253 A1 | 6/1998 |
| WO | 03013242 A1 | 2/2003 |
| WO | 03/062357 A1 | 7/2003 |
| WO | 2005/034626 | 4/2005 |
| WO | 2006/096876 | 9/2006 |

OTHER PUBLICATIONS

English Language Abstract of DE 196 45 920, May 1998.
English Language Abstract of DE 10 2005 033 845, Jan. 2007.

* cited by examiner

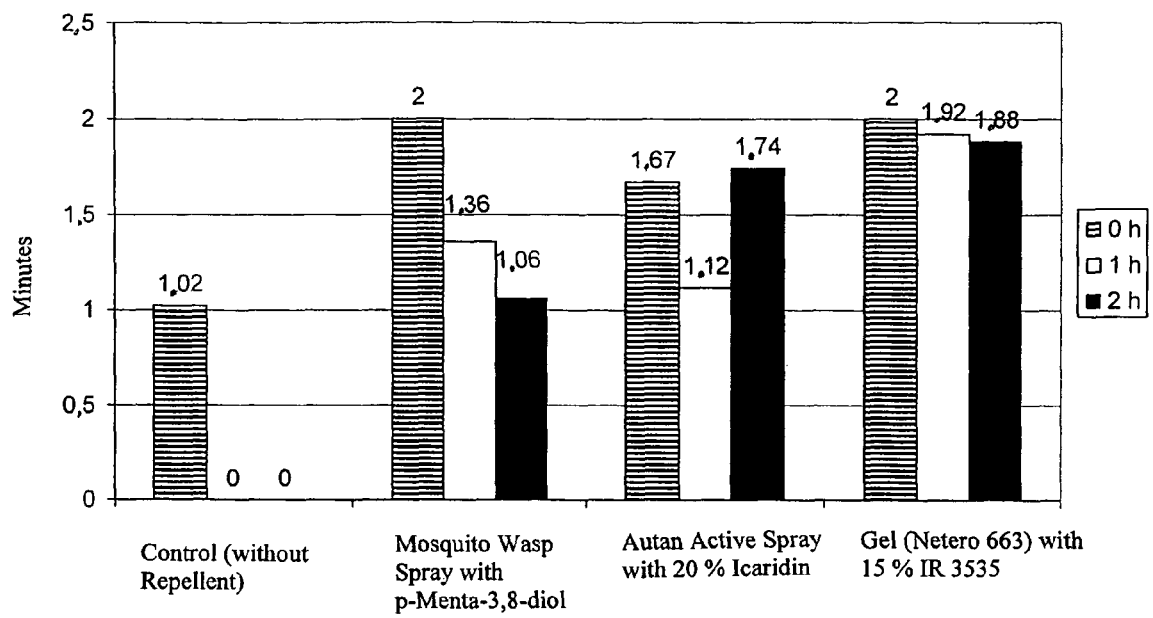

WASP REPELLENTS

CROSS-REFERENCE TO RELATED APPLICATIONS

The present application claims priority under 35 U.S.C. §119 of German Patent Application No. 10 2007 026 049.2, filed May 31, 2007, the entire disclosure whereof is expressly incorporated by reference herein.

BACKGROUND OF THE INVENTION

1. Field of the Invention

The present invention relates generally to a method of repelling wasps and to compositions which are useful in this method.

2. Discussion of Background Information

Insect repellents are preparations which are used externally to repel and/or drive away insects and also ticks and mites and are intended to prevent insects, ticks and mites from becoming active on the skin. Insect repellents are intended to protect the skin from irritation by blood-sucking or biting insects and other parasites and/or pests by repelling these before they settle on the skin, so that stings or bites do not result. Accordingly, the agents act not as contact poisons, but only as repellents since they do not kill the animals but only drive them away.

One repellent active ingredient is, e.g., 1-methylpropyl 2-(2-hydroxyethyl)-1-piperidinecarboxylate (INN: Icaridin, CAS number: 119515-38-7, Elincs number: 423-210-8), having the following structure:

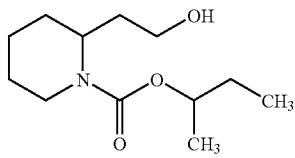 [SMILES: CCC(C)OC(=O)N1CCCCC1CCO]

Another common repellent active compound is ethyl 3-(N-n-butyl-N-acetylamino)propionate (also called repellent 3535), which is characterized by the following formula:

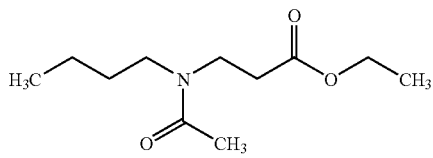

One skilled in the art is also familiar with the active repellent compound N,N-diethyl-3-methylbenzamide (trade name: meta-delphene, DEET), which is characterized by the following formula:

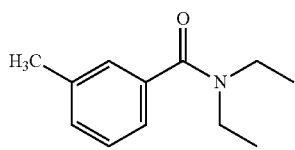

These substances have often been described as repellents against insects, in particular mosquitoes or ticks, such as, e.g., in DE 2246433, DE 19645250, DE 19645920, the entire disclosures of which are incorporated by reference herein.

In WO 2006/096876 and WO 2005/034626, the entire disclosures of which are incorporated by reference herein, dihydronepetalactones are described as repellents against insects.

Catnip or nepeta is known as a mosquito repellent and is said to have a ten times stronger repellent action against mosquitoes than conventional repellents.

DE 10 2005 033845, the entire disclosure of which is incorporated by reference herein, mentions, among others, using certain perfume ingredients to repel mosquitoes, sand flies, lice, gadflies, wasps, bees, flies and ticks.

The problem in this regard is that a repellent ingredient that is effective, e.g., against mosquitoes, does not exhibit this repellent effect against other insects or only to a limited extent.

In particular, the known insect repellents have hitherto proven unsuitable as a repellent against wasps.

Preparations with a high concentration of repellents can lead to skin irritations in individual cases, in particular among people with particularly sensitive skin. Furthermore, the active repellent ingredients have an inherent odor discernible to the human nose and not exactly appealing to others, which makes the application of insect repellent not very attractive. The repellent effect of the preparation thus extends not only to insects but furthermore to other people on occasion, if they have a keen sense of smell.

It is desirable to have available a preparation that makes it possible to repel wasps and in particular, a wasp repellent that has a reduced skin irritation potential and which gives off a fragrant perfume pleasant to the human nose.

SUMMARY OF THE INVENTION

The present invention provides a method of repelling wasps. The method comprises repelling the wasps by using a preparation which comprises (a) at least one substance selected from ethyl 3-(N-n-butyl-N-acetylamino)propionate, dihydronepetalactone, and extract of catmint, and (b) at least one compound selected from 1,3,4,6,7,8-hexahydro-4,6,6,7,8,8-hexamethyl-cyclopenta-gamma-2-benzopyran, 2,6-dimethyl-7-octen-2-ol, 1,2,3,4,5,6,7,8-octahydro-2,3,8,8-tetramethyl-2-acetonaphthone, 2-isobutyl-4-hydroxy-4-methyltetrahydropyran, 2-tert-pentylcyclohexyl acetate, 3,7-dimethyl-2,6-octadien-1-ol, 3-methyl-5-phenyl-1-pentanol, 7-acetyl-1,1,3,4,4,6 hexamethyltetraline, adipic diester, alpha-amylcinnamaldehyde, alpha-hexylcinnamaldehyde, alpha-isomethylionone, alpha-methylionone, amyl C butylphenyl methylpropional cinnamal, amyl cinnamyl alcohol, amyl salicylate, anisic alcohol, benzoin, benzyl acetate, benzyl alcohol, benzyl benzoate, benzyl cinnamate, benzyl salicylate, bergamot oil, bitter orange oil, butylphenyl methylpropional, cardamom oil, cedrol, cinnamal, cinnamyl alcohol, citral, citronellol, citronellyl methylcrotonate, lemon oil, coumarin, diethyl succinate, d-limonene, ethylenbrassylate, ethyl linalool, eugenol, evernia furfuracea extract, evernia prunastri extract, farnesol, geraniol, guaiacwood oil, heliotropin, hexyl cinnamal, hexyl salicylate, hydroxycitronellal, hydroxyisohexyl 3-cyclohexene carboxaldehyde, isoeugenol, lavender oil, lime oil, limonene, linalool, linalyl acetate, linayl acetate, mandarin oil, menthyl PCA, methyl 2-octynoate, methylbenzoate, methylcedrylketone, methyl dihydrojasmonate, methyl heptenone, myristica oil, p-t-butyl-alpha-methyldihydrocinnamic aldehyde, oil of rosemary, sweet orange oil, terpineol, tonka bean oil, triethylcitrate, and vanillin.

In one aspect of the method, component (a) may comprise ethyl 3-(N-n-butyl-N-acetylamino)propionate and/or component (b) may comprise one or more of hexyl salicylate, linayl acetate, and 2-isobutyl-4-hydroxy-4-methyltetrahydropyran.

In another aspect, the preparation may further comprise at least one additional insect repellent. For example, the preparation may comprise one or more of 1-methylpropyl 2-(2-hydroxyethyl)-1-piperidinecarboxylate (INN: Icaridin), ethyl butylacetylaminopropionate (EBAAP), and N,N-diethyl-3-methylbenzamide (DEET).

In yet another aspect of the method of the present invention, the preparation may comprise at total of not more than about 0.3% by weight, based on the total weight of the preparation, of substances which are selected from bactericides, fungicides, sporicides, preservatives, formaldehyde, and formaldehyde donors. For example, the preparation may be substantially free from these substances and in particular, substantially free from parabens.

In a still further aspect of the method, the preparation may be present as an emulsion or as a hydrodispersion gel.

In another aspect, the preparation may be applied as an impregnation medium onto a material selected from non-woven fabrics, plasters, and wipes.

In yet another aspect of the method, the preparation may be applied to the skin.

The present invention also provides a preparation for repelling wasps as set forth above (including the various aspects thereof).

In one additional aspect, the preparation may comprise from about 0.01% to about 40% by weight of component (a) and/or from about 1 ppm to about 2.5% by weight of component (b), based on the total weight of the preparation.

BRIEF DESCRIPTION OF THE DRAWINGS

The present invention is further described in the detailed description which follows, in reference to the drawings by way of non-limiting examples of exemplary embodiments of the present invention, in which drawings:
the only FIGURE is a graph which represents the results of comparative testing with several wasp repellents as described below.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

The present invention provides, inter alia, a preparation which comprises ethyl 3-(N-n-butyl-N-acetylamino)propionate, dihydronepetalactone and/or an extract of catmint (catnip) and one or more compounds selected from the perfume ingredients 1,3,4,6,7,8-hexahydro-4,6,6,7,8,8-hexamethyl-cyclopenta-gamma-2-benzopyran, 2,6-dimethyl-7-octen-2-ol, 1,2,3,4,5,6,7,8-octahydro-2,3,8,8-tetramethyl-2-acetonaphthone, 2-isobutyl-4-hydroxy-4-methyltetrahydropyran, 2-tert-pentylcyclohexylacetate, 3,7-dimethyl-2,6-octadien-1-ol, 3-Methyl-5-phenyl-1-pentanol, 7-acetyl-1,1,3,4,4,6-hexamethyltetraline, adipic diester, alpha-amyl cinnamaldehyde, alpha-hexylcinnamaldehyde, alpha-isomethylionone, alpha-methylionone, amyl C butylphenyl methylpropional cinnamal, amyl cinnamyl alcohol, amyl salicylate, anisic alcohol, benzoin, benzyl acetate, benzyl alcohol, benzyl benzoate, benzyl cinnamate, benzyl salicylate, bergamot oil, bitter orange oil, butylphenyl methylpropional, cardamom oil, cedrol, cinnamal, cinnamyl alcohol, citral, citronellol, citronellyl methylcrotonate, lemon oil, coumarin, diethyl succinate, d-limonene, ethylenbrassylate, ethyl linalool, eugenol, evernia furfuracea extract, evernia prunastri extract, farnesol, geraniol, guaiacwood oil, heliotropin, hexyl cinnamal, hexyl salicylate, hydroxycitronellal, hydroxyisohexyl 3-cyclohexene carboxaldehyde, isoeugenol, lavender oil, lime oil, limonene, linalool, linalyl acetate, linayl acetate, mandarin oil, menthyl PCA, methyl 2-octynoate, methyl benzoate, methylcedrylketone, methyl dihydrojasmonate, methyl heptenone, myristica oil, p-t-butyl-alpha-methyldihydrocinnamic aldehyde, oil of rosemary, sweet orange oil, terpineol, tonka bean oil, triethylcitrate, and vanillin for use as a wasp repellent.

The preparation is preferably a cosmetic preparation and suitable for application to the skin.

Ethyl 3-(N-n-butyl-N-acetylamino)propionate is referred to below as IR 3535 i.e., the commercial name thereof.

Dihydronepetalactones are described, e.g., in WO 2006/096876, the entire disclosure whereof is incorporated by reference herein, although the use as a wasp repellent is not disclosed herein.

Catnips (nepeta) are a plant species from the mint family (lamiaceae). According to the present invention the term "extract" encompasses all possible extracts, solutions or dispersions of nepeta plants or parts thereof.

As far as the main constituents are concerned, the essential oils contained in nepeta are citral, citronellol, geraniol and limonene, as well as nepetalactone, tannins and bitterns. The active ingredient that makes the plant so irresistible to cats is actinidin, an iridoid glycoside that is very similar to the comparable active ingredient of valerian (BOWN, 1995). The nepeta contains approx. 0.2-0.7% by weight of essential oils.

Like every other natural oil, the oleaginous extract of catnip, in particular when purified, is very difficult to spread and very polar. It is therefore uncosmetic and gives the conventional cosmetic formulae an oily, fatty phase. It is perceived to be hard to distribute. Moreover, the polar character of the extract very quickly leads to instabilities, such as, e.g., oil separation or water separation. The present invention also counteracts this disadvantage.

Wasps want to provide for their offspring and therefore need protein and substances rich in sugar in order to meet their own energy needs. That is why wasps are often attracted by cold cuts as well as sweet fruit. We often use perfume that gives off a sweet fragrance. The wasp finds us attractive and lands on our skin, flying off only when it cannot find anything to eat. Due to fear or personal experience, however, we don't wait for that, instead attacking the approaching wasp and trying to drive it away.

It has now been found in a test that certain fragrances do not attract wasps. It is surprising that fragrances from the group of the perfume ingredients 1,3,4,6,7,8-hexahydro-4,6,6,7,8,8- hexamethyl-cyclopenta-gamma-2-benzopyran, 2,6-dimethyl-7-octen-2-ol, 1,2,3,4,5,6,7,8-octahydro-2,3,8,8-tetramethyl-2-acetonaphthone, 2-isobutyl-4-hydroxy-4-methyltetrahydropyran, 2-tert-pentylcyclohexylacetate, 3,7-dimethyl-2,6-octadien-1-ol, 3-Methyl-5-phenyl-1-pentanol, 7-acetyl-1,1,3,4,4,6-hexamethyltetraline, adipic diester, alpha-amylcinnamaldehyde, alpha-hexylcinnamaldehyde, alpha-isomethylionone, alpha-methylionone, amyl C butylphenyl methylpropional cinnamal, amyl cinnamyl alcohol, amyl salicylate, anisic alcohol, benzoin, benzyl acetate, benzyl alcohol, benzyl benzoate, benzyl cinnamate, benzyl salicylate, bergamot oil, bitter orange oil, butylphenyl methylpropional, cardamom oil, cedrol, cinnamal, cinnamyl alcohol, citral, citronellol, citronellyl methylcrotonate, lemon oil, coumarin, diethyl succinate, d-limonene, ethylenbrassylate, ethyl linalool, eugenol, evernia furfuracea extract, evernia prunastri extract, farnesol, geraniol, guaiacwood oil, heliotropin, hexyl cinnamal, hexyl salicylate, hydroxycitronellal, hydroxyisohexyl 3-cyclohexene carboxaldehyde, isoeugenol, lavender oil, lime oil, limonene, linalool, linalyl acetate, linaylacetate, mandarin oil, menthyl PCA, methyl 2-octynoate, methylbenzoate, methylcedrylketone, methyl dihydrojasmonate, methyl heptenone, myristica oil, p-t-butyl-alpha-methyldihydro-cinnamic aldehyde, oil of rosemary, sweet orange oil, terpineol, tonka bean oil, triethylcitrate, and vanillin do not attract wasps.

If this preparation is applied to the skin in the form of a gel, a long-term effect is obtained.

The repellents and perfume constituents can be formulated in the gel matrix in a stable manner and are released to the environment only slowly.

Preferably, a preparation for use according to the present invention comprises one or more additional insect repellents, such as, e.g., 1-methylpropyl 2-(2-hydroxyethyl)-1-piperidinecarboxylate (INN: Icaridin), ethyl butylacetylaminopropionate (EBAAP) and/or N,N-diethyl-3-methylbenzamide (DEET).

It is advantageous according to the present invention if the preparation contains IR 3535, dihydronepetalactone and/or extracts of catnip in a total concentration of from about 0.01% to about 40% by weight, in each case based on the total weight of the preparation.

The preparation preferably contains the one or more perfume ingredients in a total concentration of from about 1 ppm to about 2.5% by weight, in each case based on the total weight of the preparation.

It also is preferred if at least one perfume ingredient from the group hexyl salicylate, linayl acetate and 2-isobutyl-4-hydroxy-4-methyltetrahydropyran is present in the preparation of the present invention.

A particularly advantageous embodiment for the purposes of the present invention is a cosmetic preparation as a hydrodispersion gel which contains about 15% by weight of IR 3535 and about 0.004% by weight of hexyl salicylate, in each case based on the total weight of the preparation.

The (preferably cosmetic) preparation according to the invention is advantageously present in the form of an aqueous or aqueous alcoholic solution, an emulsion (W/O, O/W, W/S, S/W or multiple emulsion, macro- or micro-emulsion), a dispersion, a pickering emulsion, a gel, a hydrodispersion gel or an anhydrous preparation. Preferably, the cosmetic preparation is present in the form of a hydrodispersion gel or an emulsion.

Further, the preparation can advantageously be present in the form of a thin, sprayable aqueous or aqueous alcoholic solution, in the form of a gel, as an ointment, a cream or a lotion (optionally, sprayable).

The preparation can also be advantageously used as a spray or impregnation medium for a plaster or a wipe.

The aqueous phase of the preparation according to the invention advantageously comprises one or more substances which are selected from customary cosmetic auxiliaries, such as, e.g., alcohols, particularly those of low carbon number, preferably ethanol and/or isopropanol, diols or polyols of low carbon number, and ethers thereof, preferably propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, polymers, foam stabilizers, electrolytes, self-tanning agents, and in particular, one or more thickeners which can advantageously be chosen from silicon dioxide, aluminum silicates, polysaccharides and derivatives thereof, e.g. hyaluronic acid, xanthan gum, hydroxypropylmethylcellulose, particularly advantageously from polyacrylates, preferably polyacrylates from the group of the so-called Carbopols, for example Carbopol grades 980, 981, 1382, 2984, 5984, in each case individually or in combination.

An optionally present oil phase can contain all conventional constituents of oil, fat and wax components that are used in cosmetics.

All emulsifiers and emulsifier systems known from cosmetics are examples of emulsifiers which can be used in the preparation of the present invention.

In addition to the combination of active ingredients thereof, the preparation according to the present invention can contain further cosmetically active ingredients and care ingredients such as, e.g., UV filter substances, as well as preservatives and preservation auxiliaries. Active ingredients of this type can advantageously be contained in the preparation according to the invention in concentrations of from about 0.01% to about 30% by weight, based on the total weight of the preparation.

Further examples of advantageous care substances include in particular, niacinamide, panthenol, aloe vera, hamamelis extract, polidocanol, vitamin E, vitamin E derivatives, vitamin A, vitamin A derivatives, vitamin C, vitamin C derivatives, coenzyme Q10, creatine, taurine, and alpha-glucosylrutin. These care substances are preferably present in concentrations of from about 0.1% to about 30% by weight, based on the total weight of the preparation.

Particularly preferably, the preparation according to the present invention comprises alpha-hydroxy acids and/or salts thereof as further constituents. Lactic acid/lactate and/or citric acid/citrate are preferred. The alpha-hydroxy acids and/or salts thereof are advantageously present in a concentration of from about 0.01% to about 5% by weight, based on the total weight of the preparation.

In addition to the wasp-repellent property, however, the skin tolerance and the feeling on the skin are above all decisive properties of in particular, a cosmetic product that is to be topically applied to the skin. An excellent repellent effectiveness is not worth anything if the cosmetic product leads to intolerances.

One of the intolerances by the skin that occurs most frequently is the so-called stinging effect that is unpleasantly noticeable in particular in the face. The stinging effect occurs in particular in the nasolabial region and signifies a subjective malaise of the test subjects.

In order to rule out undesirable effects of this type for cosmetics as far as possible, before the product is launched so-called stinging tests are carried out. In each case two products are tested in a direct pairwise comparison for their skin tolerance. As an internal high standard (benchmark) a commercially available product known to be tolerated by the skin is thereby used as a comparison (NIVEA Visage Day Cream normal mixed).

It has now been established in numerous tests that an important contribution to stinging is made by the parabens contained in many cosmetics, particularly when they are present in the formula in a proportion of more than about 0.3% by weight.

Parabens are used as preservatives, so it can be difficult to find a substitute.

It has now surprisingly been established that the preparations according to the invention show a very good wasp repellent effectiveness, but do not exhibit a stinging effect. The preparations according to the invention can therefore be produced preferably with a proportion of not more than about 0.3% by weight of preservatives, such as in particular parabens.

The addition of preservatives, such as, e.g., parabens, can preferably be dispensed with completely. This means that for the first time it is possible to provide repellent containing preparations which at the same time have an improved tolerance and in particular do not exhibit a stinging effect.

The preparations according to the present invention are therefore preferably substantially free from bactericidally, fungicidally and sporicidally active substances and/or free from preservatives. Furthermore, they are preferably substantially free from formaldehyde, formaldehyde donors such as diazolidinyl urea, imidazolidinyl urea and/or DMDM hydantoin and in particular substantially free from benzoic acid, p-hydroxybenzoic acid and/or the derivatives or salts thereof. The preparations according to the invention preferably contain not more than about 0.3% by weight (e.g., not more than about 0.25%, or not more than about 0.2% by weight) or in particular are substantially free from parabens, in particular substantially free from methyl paraben, ethyl paraben, propyl paraben, isopropyl paraben, butyl paraben, isobutylparaben and/or benzyl paraben. Preferably, compounds such as 2,4-dichlorobenzyl alcohol, 4-chloro-3,5-dimethylphenol, 2-bromo-2-nitropropane-1,3-diol and/or iodopropynyl butylcarbamate (IPBC) and quaternium-15 (CAS 51229-78-8), methyl-chloroisothiazolinone and/or methylisothiazolinone are not contained in the preparations according to the invention, either, or only in proportions of not more than about 0.3% by weight (e.g., not more than about 0.25%, or not more than about 0.2% by weight).

The preparations according to the present invention are particularly preferably substantially paraben-free.

As used herein and in the appended claims, "substantially free from" means a concentration of less than about 0.1% by weight (e.g., not more than about 0.05% by weight), based on the total weight of the preparation. The proportion of the aforementioned substances and in particular parabens is preferably 0% by weight.

As in particular a cosmetic preparation, the preparation according to the invention is advantageously suitable as a substance for topical application. However, the preparation also may show a distinct wasp-repellent effect as a preparation applied to objects and clothing or sprayed into the air.

The use of the preparation according to the invention as a prophylaxis for wasp stings is in particular according to the invention.

The preparation according to the invention was tested for use as a wasp repellent.

The formula (Netero 663) according to the invention comprises:

| INCI | Netero 663 |
|---|---|
| Aqua | 53.275 |
| Cyclomethicone | 8 |
| Glycerin | 9 |
| Sodium hydroxide | 0.2 |
| Alcohol denat. | 10 |
| Ethyl butylacetylaminopropionate | 15 |
| Acrylates/C10-30 alkyl acrylate crosspolymer | 0.2 |
| Carbomer | 0.2 |
| Perfume* | 0.2 |
| CI 42090 | 0.4 |
| Aloe barbadensis | 0.025 |
| Chrondrus crispus | 0.2 |
| Hamamelis virginiana distillate | 0.1 |
| Sodium polyacrylate | 0.2 |
| Cyclomethicone + Dimethiconol | 1 |
| Methylpropanediol | 2 |

*perfume contains: 34.5% limonene and 6.5% linalool

The tests were carried out with two substances in each case on two consecutive days. In each case 6 people took part in the test with one substance. Before the test, respectively 20 freshly caught, completely active wasps (paravespula vulgaris) were placed in four conventional fly cages with one arm opening and closure of cotton. Immediately before the test the left hand and the left arm of each test subject were rubbed or sprayed up and down with the respective test substance. Then the substance was allowed to penetrate briefly (approx. 1-2 minutes). Then a drop of forest honey was placed on the surface of the lower arm just above the wrist on both arms. This forest honey had proven in preliminary tests to be extremely attractive to this type of wasp. Then each test subject placed his right untreated arm into the cage as a control. This untreated arm area was observed as a control.

The time was recorded until at least 3 wasps had firmly landed on the honey and started to eat it. These times were entered into the record. 2 minutes was chosen as the exclusion time. Directly thereafter each of the test subjects placed its sprayed arm into the cage and it was recorded in turn how long it took for three wasps to start eating. This was repeated after one hour—but without spraying new repellent substance onto the skin. This was repeated again after 2 hours.

The only FIGURE shows the test results that substantiate that the preparation according to the invention shows a stronger wasp repellent property than the known insect repellents (Autan, Mosquito). After 2 minutes on average (exclusion time), no wasps had settled on the arm with the preparation according to the invention. After one hour 3 wasps had settled on the arm with Autan already within 1.12 minutes. After 2 hours the value was somewhat better, but the protection was never as good as with Netero 633. This preparation with 15% IR 3535 always exhibited the best protection from wasps.

The following examples are provided to further illustrate the present invention without limiting it in any way. The data always refer to % by weight, unless stated otherwise.

| W/O Emulsions | | | | | |
|---|---|---|---|---|---|
| | 1 | 2 | 3 | 4 | 5 |
| Triglycerin diisostearate | 1.0 | 0.5 | 0.25 | 2.0 | 3.0 |
| Diglycerin dipolyhydroxystearate | 1.0 | 1.5 | 1.75 | 3.0 | 2.0 |
| Paraffin oil | 12.5 | 10.0 | 8.0 | 5.0 | 17.5 |
| Petrolatum | 8.0 | 6.0 | 5.0 | 12.0 | 2.5 |
| Hydrogenated cocoglycerides | 2.0 | 1.0 | 2.5 | 5.0 | 0.25 |
| Decyl oleat | 0.5 | 0.75 | 1.0 | 2.0 | 0.25 |
| Octyldodecanol | 0.5 | 1.0 | 0.75 | 3.0 | 0.25 |
| Aluminum stearate | 0.4 | 0.3 | 0.6 | 1.0 | 0.05 |
| Dicaprylyl carbonate | 0.1 | 0.05 | 0.15 | 0.5 | 1.0 |
| Hydrogenated castor oil | 0.5 | 0.75 | 1.0 | 2.5 | 5.0 |
| Iminodisuccinic acid | 0.5 | — | — | — | 0.1 |
| Magnesium sulfate | 0.5 | 0.6 | 0.5 | 0.7 | 1.0 |
| Glycerin | 3.0 | 5.0 | 10.0 | 15.0 | 1.5 |
| Ethyl 3-(N-n-butyl-N-acetylamino)propionate | 5 | 15 | 8 | 10 | 3 |
| Hexyl salicylate | 0.3 | 0.4 | 0.25 | 0.15 | 150 ppm |
| Ethanol | 2.0 | — | 5.0 | — | — |
| Caprylic/capric acid triglyceride | 2.0 | 2.5 | 3.0 | 5.0 | 0.5 |
| Methylparaben | 0.4 | 0.15 | 0.05 | 0.3 | 0.4 |
| Propylparaben | 0.3 | 0.4 | 0.25 | 0.15 | — |
| Fucose | 0.5 | 1.5 | 1 | 0.5 | 0.1 |
| Raffinose | 0.5 | 0.75 | 1 | 0.35 | 0.1 |
| Galactose | 0.5 | 0.35 | 1 | 1.75 | 0.1 |
| Water | ad 100 | ad 100 | ad 100 | ad 100 | ad 100 |

| W/O Emulsions | | | | | |
|---|---|---|---|---|---|
| | 6 | 7 | 8 | 9 | 10 |
| PEG-30 Dipolyhydroxystearate | — | 0.5 | 0.25 | — | 3.0 |
| Lanolin Alcohol | 1.0 | 1.5 | 1.75 | 3.0 | 2.0 |
| Paraffin oil | 12.5 | 10.0 | 8.0 | 5.0 | 17.5 |
| Petrolatum | 8.0 | 6.0 | 5.0 | 12.0 | 2.5 |
| Hydrogenated cocoglycerides | 2.0 | 1.0 | 2.5 | 5.0 | 0.25 |
| Hydrogenated polyisobutene | 0.5 | 0.75 | 1.0 | 2.0 | 0.25 |
| Octyldodecanol | 0.5 | 1.0 | 0.75 | 3.0 | 0.25 |
| Aluminum stearate | 0.4 | 0.3 | 0.6 | 1.0 | 0.05 |
| Dicaprylyl carbonate | 0.1 | 0.05 | 0.15 | 0.5 | 1.0 |
| Hydrogenated castor oil | 0.5 | 0.75 | 1.0 | 2.5 | 5.0 |
| Ethyl 3-(N-n-butyl-N-acetylamino)propionate | 12.5 | 1.0 | 7.5 | 10 | 5 |
| Magnesium sulfate | 0.5 | 0.6 | 0.5 | 0.7 | 1.0 |
| Glycerin | — | 5.0 | — | 15.0 | 5.5 |
| Tetrasodium iminosuccinate | 1.5 | 0.6 | 3.0 | 0.4 | 1.0 |
| Linayl acetate | 0.15 | 15 ppm | 0.5 | 0.0025 | 0.0065 |
| 1,3-Butylene glycol | — | — | 5.0 | — | 7.5 |
| Caprylic/capric acid triglyceride | 2.0 | 2.5 | 3.0 | 5.0 | 0.5 |
| Methylparaben | 0.4 | 0.15 | 0.05 | 0.3 | 0.4 |
| Mannose | 0.5 | 1.5 | 1 | 0.5 | 0.1 |
| Rhamnose | 0.75 | 0.75 | 1.25 | 0.35 | 0.1 |
| Fucose | 1.5 | 0.35 | 1 | 1.75 | 0.1 |
| Propylparaben | 0.3 | 0.4 | 0.25 | 0.15 | — |
| Water | ad 100 | ad 100 | ad 100 | ad 100 | ad 100 |

| W/S Emulsions | | | | | |
|---|---|---|---|---|---|
| | 11 | 12 | 13 | 14 | 15 |
| Cetyldimethicone copolyol | 1.0 | — | — | 3.0 | 5.0 |
| Cylomethicone + dimethicone copolyol | 10.0 | 12.5 | 25 | — | — |
| Cyclomethicone | 12.5 | 15 | 28.0 | 25.0 | 17.5 |
| Dimethicone | 5.0 | 13.0 | 5.0 | 12.0 | 15.0 |
| Hydrogenated polyisobutene | 0.5 | 0.75 | 1.0 | 2.0 | 0.25 |
| Octyldodecanol | 0.5 | 1.0 | 0.75 | 3.0 | 0.25 |
| Panthenol | 0.5 | 1.0 | 0.75 | 0.25 | 0.1 |
| Magnesium chloride | 2.0 | 0.6 | 2.5 | 0.7 | 1.0 |
| Glycerin | 25.0 | 5.0 | 10.0 | 15.0 | 57.5 |
| Ethyl 3-(N-n-butyl-N-acetylamino)propionate | 6 | 10 | 12 | 1.5 | 5.0 |
| Hexyl salicylate | 0.3 | 0.04 | 0.25 | 0.12 | 150 ppm |
| Methylparaben | 0.4 | 0.1 | 0.05 | 0.3 | 0.4 |
| Butylene glycol | — | 5.0 | — | — | 7.5 |
| Propylparaben | 0.3 | 0.4 | 0.25 | 0.15 | — |
| Cetyldimethicone | 0.5 | — | 0.7 | — | — |
| Iodopropynyl butylcarbamate | — | — | 0.05 | — | 0.1 |
| Fucose | 0.5 | 1.5 | 1 | 0.5 | 0.1 |
| Raffinose | 0.5 | 0.75 | 1 | 0.35 | 0.1 |
| Galactose | 0.5 | 0.35 | 1 | 1.75 | 0.1 |

|  | | | | | |
|---|---|---|---|---|---|
| Modified starch | — | 2.5 | — | 0.15 | — |
| Water | ad 100 | ad 100 | ad 100 | ad 100 | ad 100 |

O/W Emulsions

|  | 16 | 17 | 18 | 19 | 20 |
|---|---|---|---|---|---|
| Glyceryl stearate citrate | 2 | — | — | — | — |
| Glyceryl stearate | — | 5 | 2 | 3 | — |
| PEG-40 stearate | — | — | 1 | — | — |
| Triglycerin methylglucose distearate | — | — | — | — | 3 |
| Sorbitan stearate | — | — | — | — | 1 |
| Cetearyl glucoside | — | — | — | 2 | — |
| Behenyl alcohol | — | — | — | — | 1 |
| Stearyl alcohol | 2 | 1 | — | — | — |
| Cetylstearyl alcohol | — | — | 2 | — | — |
| Hydrogenated coconut oil glycerides | 2 | — | — | 1 | — |
| Shea butter | — | 2 | — | — | — |
| Butylene glycol dicaprylate/dicaprate | 1 | — | — | — | — |
| Caprylic/capric triglyceride | — | 4 | — | — | 1 |
| Ethylhexyl coconut fatty acid esters | 3 | — | — | — | — |
| Octyldodecanol | — | — | 5 | 8 | — |
| Mineral oil | 8 | 1 | — | — | 5 |
| Ethyl 3-(N-n-butyl-N-acetylamino)propionate | 8 | 3 | 10 | 12 | 7.5 |
| Petrolatum | 4 | — | — | 2 | — |
| Octamethyltetrasiloxane | 5 | 1 | 3 | 1 | 3 |
| Dimethylpolysiloxane | — | 3 | 1 | 3 | 2 |
| Dicaprylylcarbonate | 10 | 1 | 8 | 5 | 2 |
| Glycerin | 3.0 | — | 25 | 12.5 | 30 |
| Methylparaben | 0.3 | — | — | 0.2 | 0.4 |
| Galactose | 0.15 | 0.1 | 1 | 1.5 | 0.25 |
| N-Acetylglucosamine | 0.3 | 0.1 | 1.25 | 2.5 | 0.75 |
| Fucose | 1.5 | 0.1 | 3 | 0.75 | 0.25 |
| Iodopropynyl butylcarbamate | 0.1 | 0.2 | 0.2 | 0.05 | — |
| Linayl acetate | 0.15 | 15 ppm | 0.5 | 0.0025 | 0.0065 |
| Water | ad 100 | ad 100 | ad 100 | ad 100 | ad 100 |

O/W Emulsions

|  | 21 | 22 | 23 | 24 | 25 |
|---|---|---|---|---|---|
| Glyceryl stearate citrate | 5 | — | — | — | — |
| Glyceryl stearate | — | 5 | — | — | — |
| PEG 40 stearate | — | 2 | — | — | — |
| Polyethylenglycol(21)stearylether | — | — | 2 | — | — |
| Polyethylenglycol(2)stearylether | — | — | 1 | — | — |
| Cetearyl glucoside | — | — | — | 2 | — |
| Stearic acid | — | — | — | — | 2.5 |
| Behenyl alcohol | — | — | — | — | 2 |
| Stearyl alcohol | 2 | 1 | — | 5 | — |
| Cetylstearyl alcohol | — | — | 2 | — | 1 |
| Hydrogenated coconut oil glycerides | 2 | — | — | 3 | 1 |
| Butylene glycol dicaprylate/dicaprate | 1 | — | 8 | — | 2 |
| Caprylic/capric triglyceride | — | 4 | 2 | — | — |
| Ethylhexyl coconut fatty acid esters | 3 | 6 | — | — | 2 |
| Octyldodecanol | — | — | 1 | 9 | — |
| Mineral oil | 9 | 1 | 1 | 1 | 3 |
| Petrolatum | 4 | 2 | 5 | 0.5 | 0.75 |
| Glycerin | 7.5 | 15 | 65 | 25 | — |
| Ethyl 3-(N-n-butyl-N-acetylamino)propionate | 3.5 | 3 | 8.5 | 25 | 15 |
| Raffinose | 0.15 | 0.1 | 1 | 1.5 | 0.25 |
| N-Acetylglucosamine | 0.3 | 0.1 | 1.25 | 2.5 | 0.75 |
| Fucose | 1.5 | 0.1 | 3 | 0.75 | 0.25 |
| Octamethyltetrasiloxane | — | 1 | 2 | 5 | — |
| Dimethylpolysiloxane | 0.5 | 0.75 | 1.25 | — | 1 |
| Dicaprylyl carbonate | 6 | 2 | 10 | 0.5 | 4 |
| Methylparaben | 0.3 | — | 0.1 | — | 0.05 |
| 2-Isobutyl-4-hydroxy-4-methyltetrahydropyran | 0.3 | 60 ppm | 0.0125 | 0.065 | 0.75 |
| Iodopropynyl butylcarbamate | 0.1 | 0.2 | 0.1 | 0.2 | 0.15 |
| Water | ad 100 | ad 100 | ad 100 | ad 100 | ad 100 |

Hydrodispersion Gels

|  | 26 | 27 | 28 | 29 | 30 |
|---|---|---|---|---|---|
| Silicone oil, cyclic | 8 | 10 | 5 | 3 | — |
| Silicone oil, linear | — | — | — | — | 3 |
| Dimethiconol | 1 | 2 | 3 | — | 3 |
| Ethanol | 10 | 15 | 7.5 | 5 | 3 |

-continued

| | | | | | |
|---|---|---|---|---|---|
| Ethyl 3-(N-n-butyl-N-acetylamino)propionate | 15 | 5 | 15 | 20 | 30 |
| Sodium polyacrylate | 0.2 | 0.3 | 0.3 | 0.4 | 0.10 |
| Methylpropanediol | 2 | 3 | 4 | 5 | — |
| Glycerin | 9 | 15 | 5 | 7.5 | 25 |
| Carbomer | 0.2 | 0.3 | 0.2 | 0.4 | 0.15 |
| Acrylates/C10-30Alkyl Acrylate Crosspolymer | 0.2 | 0.15 | 0.3 | 0.4 | 0.10 |
| Carrageenan (Chondrus Crispus) | — | — | — | — | 2 |
| *Hamamelis* extract | 0.1 | 0.2 | 0.3 | 0.4 | — |
| 2-Isobutyl-4-hydroxy-4-methyltetrahydropyran | 0.3 | 60 ppm | 0.0125 | 0.065 | 0.75 |
| Perfume | q.s. | q.s. | q.s. | q.s. | q.s. |
| Colorant | q.s. | q.s. | q.s. | q.s. | q.s. |
| Water | ad 100 | ad 100 | ad 100 | ad 100 | ad 100 |
| *Aloe vera* extract | 0.1 | 0.2 | 0.5 | 0.2 | 1.0 |

Ethanol Sprays

| | 31 | 32 | 33 | 34 | 35 |
|---|---|---|---|---|---|
| Glycerin | 9 | 15 | 20 | 5 | 7.5 |
| Ethanol | 42.5 | 45 | 40 | 35 | 25 |
| Ethyl 3-(N-n-butyl-N-acetylamino)propionate | 15 | 10 | 5 | 20 | 25 |
| Water | ad 100 | ad 100 | ad 100 | ad 100 | ad 100 |
| PPG-1-PEG-9 Laurylglycolether | 0.4 | 0.2 | 0.6 | 1.0 | 5 |
| Methylheptenone | 0.3 | 0.025 | 0.125 | 150 ppm | 0.75 |
| *Hamamelis* extract | 0.1 | 0.2 | 0.35 | 0.4 | — |
| *Aloe vera* extract | 0.025 | 0.2 | 0.5 | 0.02 | 1.0 |

O/W Emulsions, light

| | 36 | 37 | 38 | 39 | 40 |
|---|---|---|---|---|---|
| Ethyl 3-(N-n-butyl-N-acetylamino)propionate | 15 | 10 | 5 | 20 | 30 |
| Glyceryl stearate | 1 | 1 | 2 | 5 | 2 |
| Cetearyl alcohol + sodium cetearyl sulfate | 3 | 4 | 5 | 2 | 8 |
| Phenoxyethanol | 0.5 | 0.6 | 0.75 | 1.0 | 0.35 |
| Xanthan Gum | 0.5 | 0.75 | 0.35 | 0.4 | 1.0 |
| Menthyl PCA | 0.5 | 2.5 | 1.5 | 2.0 | 0.25 |
| *Hamamelis* extract | 0.1 | 0.2 | 0.35 | 0.4 | — |
| *Aloe vera* extract | 0.025 | 0.2 | 0.5 | 0.02 | 1.0 |
| Dicaprylyl carbonate | 5 | 7.5 | 3 | 10 | 2.5 |
| Caprylic/capric triglyceride | 5 | 7.5 | 3 | 2.1 | 1.8 |
| Silicone oil, linear | 3 | 2 | — | 0.75 | 5 |
| Caprylyl glycol | 0.5 | — | 0.3 | — | 0.1 |
| Ethanol | 2.5 | 3.5 | 5 | 1.5 | — |

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A method of repelling wasps, wherein the method comprises repelling the wasps by using a preparation comprising about 15% by weight of ethyl 3-(N-n-butyl-N-acetylamino) propionate and further comprising hexyl salicylate, linalool and limonene.

2. The method of claim 1, wherein the preparation comprises about 0.004% by weight of hexyl salicylate.

3. The method of claim 2, wherein the preparation comprises 0.079% by weight of limonene and 0.013% by weight of linalool.

4. The method of claim 1, wherein the preparation further comprises at least one compound selected from 1,3,4,6,7,8-hexahydro-4,6,6,7,8,8-hexamethyl-cyclopenta-gamma-2-benzopyran, 2,6-dimethyl-7-octen-2-ol, 1,2,3,4,5,6,7,8-octahydro-2,3,8,8-tetramethyl-2-acetonaphthone, 2-isobutyl-4-hydroxy-4-methyltetrahydropyran, 2-tert-pentylcyclohexyl acetate, 3,7-dimethyl-2,6-octadien-1-ol, 3-methyl-5-phenyl-1-pentanol, 7-acetyl-1,1,3,4,4,6 hexamethyltetraline, adipic diester, alpha-amylcinnamaldehyde, alpha-hexylcinnamaldehyde, alpha-isomethylionone, alpha-methylionone, amyl C butylphenyl methylpropional cinnamal, amyl cinnamyl alcohol, amyl salicylate, anisic alcohol, benzoin, benzyl acetate, benzyl alcohol, benzyl benzoate, benzyl cinnamate, benzyl salicylate, bergamot oil, bitter orange oil, butylphenyl methylpropional, cardamom oil, cedrol, cinnamal, cinnamyl alcohol, citral, citronellol, citronellyl methylcrotonate, lemon oil, coumarin, diethyl succinate, ethylenbrassylate, ethyl linalool, eugenol, evernia furfuracea extract, evernia prunastri extract, farnesol, geraniol, guaiacwood oil, heliotropin, hexyl cinnamal, hydroxycitronellal, hydroxyisohexyl 3-cyclohexene carboxaldehyde, isoeugenol, lavender oil, lime oil, linalyl acetate, linayl acetate, mandarin oil, menthyl PCA, methyl 2-octynoate, methylbenzoate, methylcedrylketone, methyl dihydrojasmonate, methyl heptenone, myristica oil, p-t-butyl-alpha-methyldihydrocinnamic aldehyde, oil of rosemary, sweet orange oil, terpineol, tonka bean oil, triethylcitrate, and vanillin.

5. The method of claim 1, wherein the preparation further comprises at least one additional insect repellent.

6. The method of claim 5, wherein the at least one additional insect repellent comprises at least one of 1-methylpropyl 2-(2-hydroxyethyl)-1-piperidinecarboxylate (INN: Icaridin), and N,N-diethyl-3-methylbenzamide (DEET).

7. The method of claim 1, wherein the preparation comprises not more than a total of about 0.3% by weight of substances which are selected from bactericides, fungicides, sporicides, preservatives, formaldehyde, and formaldehyde donors.

8. The method of claim 1, wherein the preparation is free from bactericides, fungicides, sporicides, preservatives, formaldehyde, and formaldehyde donors.

9. The method of claim 1, wherein the preparation is free from parabens.

10. The method of claim 1, wherein the preparation is present as a hydrodispersion gel.

11. The method of claim 1, wherein the preparation is present as an emulsion.

12. The method of claim 1, wherein the preparation is applied as an impregnating medium onto a material selected from non-woven fabrics, plasters, and wipes.

13. The method of claim 1, wherein the preparation is applied to skin.

* * * * *